US011191585B2

(12) United States Patent
Bannino

(10) Patent No.: US 11,191,585 B2
(45) Date of Patent: Dec. 7, 2021

(54) ELECTROSURGICAL APPARATUS TO PERFORM A TISSUE CUT ON THE BODY OF A HUMAN OR ANIMAL PATIENT

(71) Applicant: OTECH INDUSTRY SRL, Turin (IT)

(72) Inventor: Alberto Bannino, Turin (IT)

(73) Assignee: OTECH INDUSTRY SRL, Turin (IT)

( * ) Notice: Subject to any disclaimer, the term of this patent is extended or adjusted under 35 U.S.C. 154(b) by 882 days.

(21) Appl. No.: 15/746,727

(22) PCT Filed: Jul. 22, 2016

(86) PCT No.: PCT/IB2016/054369
§ 371 (c)(1),
(2) Date: Jan. 22, 2018

(87) PCT Pub. No.: WO2017/013624
PCT Pub. Date: Jan. 26, 2017

(65) Prior Publication Data
US 2018/0193083 A1    Jul. 12, 2018

(30) Foreign Application Priority Data

Jul. 22, 2015  (IT) .................. 102015000037078

(51) Int. Cl.
*A61B 18/12*  (2006.01)
*A61B 18/14*  (2006.01)
(Continued)

(52) U.S. Cl.
CPC ...... *A61B 18/1206* (2013.01); *A61B 18/1233* (2013.01); *A61B 18/1402* (2013.01);
(Continued)

(58) Field of Classification Search
CPC ............ A61B 18/1206; A61B 18/1233; A61B 18/1402; A61B 18/16; A61B 18/1477;
(Continued)

(56) References Cited

U.S. PATENT DOCUMENTS 6,039,734 A * 3/2000 Goble .................... A61B 18/12
606/41
10,327,831 B2 * 6/2019 Bannino .............. A61B 18/042
(Continued)

FOREIGN PATENT DOCUMENTS

EP      1 174 093 A1   1/2002
EP      2 826 434 A1   1/2015
WO    2014/181279 A1  11/2014

OTHER PUBLICATIONS

International Preliminary Report on Patentability from International Application No. PCT/IB2016/05436, dated Nov. 7, 2017.
(Continued)

*Primary Examiner* — Linda C Dvorak
*Assistant Examiner* — Annabeth E Rodriguez
(74) *Attorney, Agent, or Firm* — Merchant & Gould P.C.

(57) ABSTRACT

An electrosurgical apparatus performs a cut or incision on epithelial tissue of the body of a human or animal patient. The apparatus includes a generator system configured to generate a radio-frequency electric signal, and a hand piece held by an operator and having an end provided with a single active electrode electrically connected to the generator system. The electric signal generates a cut or an incision when the active electrode comes into contact with epithelial tissue of the body. The electric signal has a power ranging from 0.5 W-20 W and a frequency ranging from 40 kHz-90 kHz. The energy emitted by the signal is transferred from the active electrode to the tissue of the body through capacitive coupling. The tissue is cut at a peripheral temperature ranging from 45° C.-60° C. The electric circuit is closed to ground through a capacitive effect, as the apparatus does not use a return plate.

11 Claims, 4 Drawing Sheets

(51) Int. Cl.
*A61B 18/16* (2006.01)
*A61B 18/00* (2006.01)
(52) U.S. Cl.
CPC .......... *A61B 18/16* (2013.01); *A61B 18/1477* (2013.01); *A61B 2018/0072* (2013.01); *A61B 2018/00178* (2013.01); *A61B 2018/00601* (2013.01); *A61B 2018/00702* (2013.01); *A61B 2018/00726* (2013.01); *A61B 2018/00732* (2013.01); *A61B 2018/147* (2013.01)
(58) Field of Classification Search
CPC  A61B 2018/00178; A61B 2018/00601; A61B 2018/00702; A61B 2018/0072; A61B 2018/00726; A61B 2018/00732; A61B 2018/147
See application file for complete search history.

(56) References Cited

U.S. PATENT DOCUMENTS

| 2002/0022836 | A1* | 2/2002 | Goble | A61B 18/12 |
| | | | | 606/34 |
| 2003/0014051 | A1* | 1/2003 | Woloszko | A61B 18/1477 |
| | | | | 606/46 |
| 2004/0030328 | A1 | 2/2004 | Eggers et al. | |

OTHER PUBLICATIONS

International Search Report and Written Opinion from International Application No. PCT/IB2016/05436, dated 78 Nov. 2016.

* cited by examiner

ELECTROSURGICAL APPARATUS TO PERFORM A TISSUE CUT ON THE BODY OF A HUMAN OR ANIMAL PATIENT

This application is a National Stage Application of International Application No. PCT/IB2016/054369, filed Jul. 22, 2016, which claims benefit of Serial No. 102015000037078, filed Jul. 22, 2015 in Italy and which applications are incorporated herein by reference. To the extent appropriate, a claim of priority is made to each of the above disclosed applications.

TECHNICAL FIELD

The present invention relates to an electrosurgical apparatus, in particular for performing a tissue cut or incision on the body of a human or animal patient.

BACKGROUND ART

In this field, it is widely known to use electrosurgical apparatuses comprising a generator system configured to generate a radio-frequency electric signal, and a handpiece to be held by an operator and comprising an end fitted with an active electrode electrically connected to said generator system.

However, apparatuses of the above-mentioned kind suffer from a few drawbacks.

EP 1 174 093 A1 discloses an apparatus which, in order to cut a patient's epithelial tissue, uses an electric signal applied to the cutting electrode which has the following electric characteristics: a high-frequency or radio-frequency signal comprised between 20 kHz and 20 MHz, an active voltage comprised between 5V and 1000V, with a mean power comprised between tens of milliwatts and tens of watts. Moreover, this apparatus needs to use, in addition to the active electrode, also another electrode arranged proximal to the active electrode. This type of apparatus has a peripheral temperature of 40° C. to 500° C., thus significantly increasing the sensation of pain. Furthermore, since the temperature may even reach values in excess of 90° C., a coagulation effect may develop and cell necrotization may be promoted, particularly in soft tissues, e.g. mucosae.

US 2004/0030328 describes an electrosurgical apparatus that adopts a return plate. This document also specifies that the frequency of the signal applied to the active electrode is not lower than 100 kHz, with a peak-to-peak voltage of approx. 1 kV, which may even reach 1.4 kV.

In general, traditional acusectors operate at frequencies around 500 kHz, because at lower frequencies, typically around 350 kHz, the phenomenon of muscle tetanization or faradic effect occurs. Moreover, traditional acusectors use a return electrode or return plate that closes the electric circuit through the patient's body. At the above-specified frequencies, this phenomenon may lead to in-depth penetration of the electric signal, resulting in muscle tetanization.

With traditional devices, high power is required for using frequencies around 500 kHz for tissue cutting applications, since the higher the frequency the less the electric signal is diffused in the tissue.

From patent application WO 2014/181279 A1 an electrosurgical apparatus is also known which comprises a generator system configured to generate a radio-frequency signal, and a handpiece to be held by an operator. Said handpiece comprises a first end connected to an electrically active electrode, in turn connected to the generator system. The signal can polarize the active electrode in order to generate a luminescent plasma discharge in the atmosphere when the active electrode comes near a tissue mass, without propagation of electric current through the patient's body. This application also specifies that the apparatus is suitable for performing only an abrasion, not a cut, on the tissue, in addition to being wholly ineffective if placed into direct contact with the tissue mass of the patient; therefore, the described device cannot be used for performing a cut or an incision on the skin without first undergoing some modifications.

SUMMARY OF THE INVENTION

It is one object of the present invention to provide an electrosurgical apparatus which can overcome the drawbacks of the prior art.

It is a further object of the present invention to provide an improved and reliable electrosurgical apparatus that can nevertheless be produced in a simple and economical manner.

According to the present invention, this and other objects are achieved through an electrosurgical apparatus.

It is to be understood that the appended claims are an integral part of the technical teachings provided in the following detailed description of the invention.

BRIEF DESCRIPTION OF THE DRAWINGS

Further features and advantages of the present invention will become apparent from the following detailed description, which is supplied by way of non-limiting example with particular reference to the annexed drawings, wherein.

DETAILED DESCRIPTION OF THE INVENTION

Figure 1:
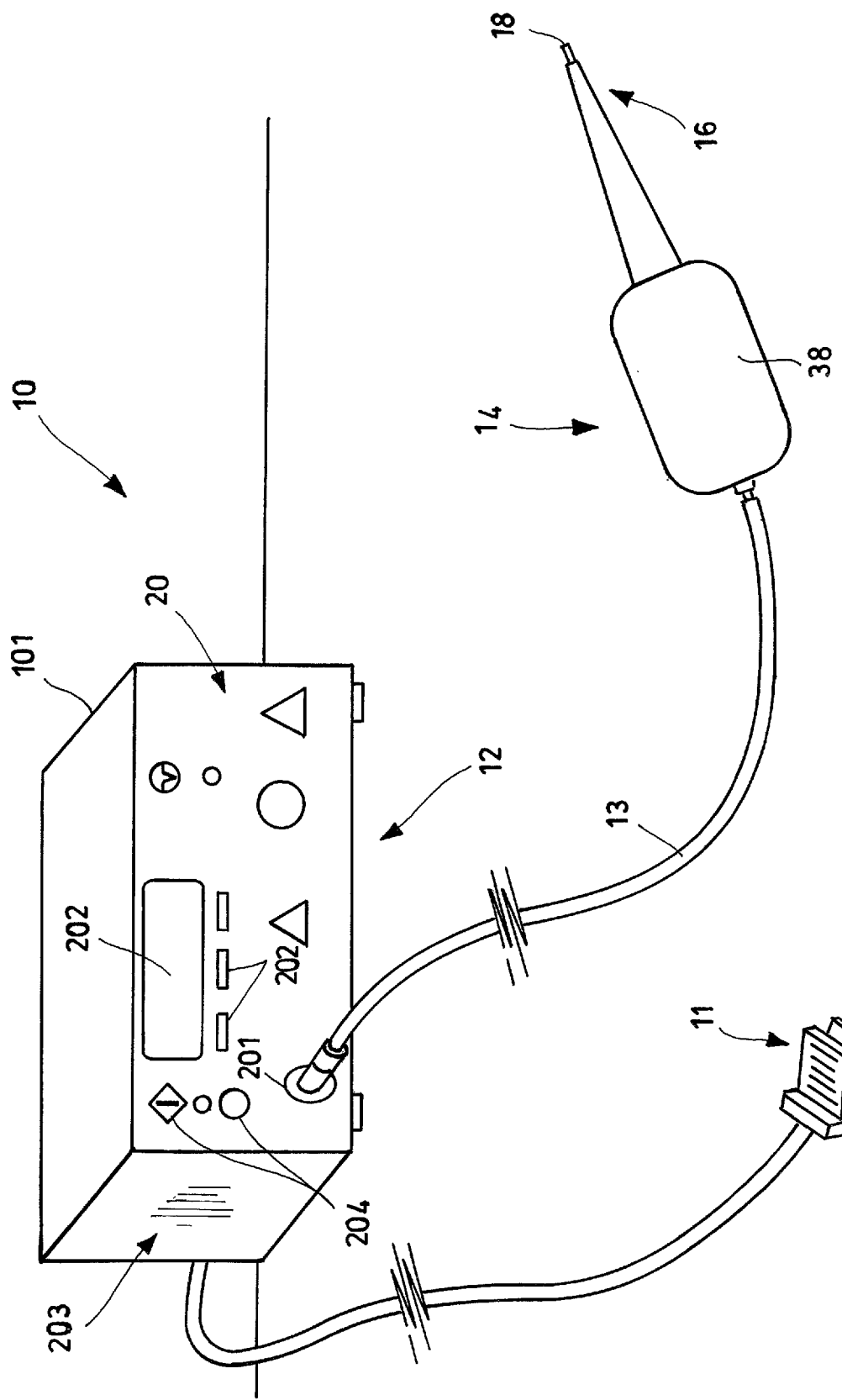
FIG. 1 is a perspective view of the apparatus, comprising the handpiece and the generator, in accordance with an illustrative embodiment of the present invention.

With reference to the embodiment shown in the drawings, electrosurgical apparatus 10 according to the present invention is particularly suited for the execution of a tissue cut or incision "C" on body "B" of a human or animal patient.

Apparatus 10 according to the present invention comprises: a generator system 12 configured to generate a radio-frequency electric signal; a handpiece 14 to be held by an operator and comprising an end 16. End 16 is provided with a single active electrode 18 electrically connected to said generator system 12.

The electric signal generated by generator system 12 is configured to generate a tissue cut or incision "C" when said active electrode 18 comes into contact with the tissue of body "B" of the patient. The execution of cut or incision "C" occurs through thermal effect.

Apparatus 10, in particular generator system 12, is configured to generate an electric signal having a power ranging from 0.5 W to 20 W and a frequency ranging from 40 kHz to 90 kHz.

The same electric signal is configured in such a way that the energy emitted is transferred from active electrode 18 to the tissue of body "B" through capacitive coupling. In particular, cut "C" is made by exploiting the potential difference existing between active electrode 18 and patient's body "B", thus effecting an energy transfer that vaporizes, through thermal effect, the epithelial cells that come into contact with active electrode 18.

Furthermore, the apparatus according to the present invention generates an electric signal configured in such a way that tissue cut "C" is executed at a peripheral temperature ranging from 45° C. to 60° C.

Through the effect of thermal dissipation due to the atmospheric air that surrounds active electrode 18, and adapted to generate the capacitive coupling, the energy transmitted to patient's body "B", has a lower temperature than conventional acusectors which normally operate in cutting mode at temperatures in excess of 100° C., and which typically cause cell necrotization, with the risk of producing keloids in the patient's body. On the contrary, the reduced temperature induced by using apparatus 10 according to the present invention, is sufficient to obtain tissue vaporization or sublimation, thus generating cut "C" without causing the explosion of the cells making up the tissue. In particular, the air around electrode 18 ionizes, thus creating a plasma microflow capable of effectively making a cut or an incision "C" on the tissue of body "B".

Apparatus 10 according to the present invention is configured in such a way that, during the execution of cut "C", the resulting electric circuit—starting from active electrode 18—is closed to ground through a capacitive effect, as apparatus 10 does not use a return plate.

It must be pointed out that, following the contact established between active electrode 18 and the tissue of body "B", the energy associated with the electric signal generated by generator system 12 will still persist, thus allowing the execution of the cut or incision "C" on the tissue of body "B".

As mentioned above, electric charges and currents are typically generated in electrosurgical apparatuses which tend to flow through the human body. For this reason, in such other types of devices a return electrode or dissipation plate must be applied to the patient's body, generally on the side opposite to the region where handpiece 14 is used. According to the present invention, instead, since there is a capacitive coupling both between active electrode 18 and patient's body "B" and between patient's body "B and the ground, the electric circuit is closed to ground. In the solution according to the present invention it is no longer necessary to use a return electrode or dissipation plate.

In a preferred but non-limiting embodiment, said generator system 12 is adapted to generate an electric signal having the following parameters: current intensity of approx. 0.0005 A; frequency of approx. 50 kHz, and a duty cycle duration approximately ranging from 10 μs to 30 μs.

The peripheral temperature obtainable through the use of a signal having the above-mentioned characteristics is approx. 50° C. A further advantage offered by the use of an apparatus 10 according to the present invention is that the low temperature transferred to the tissues ensures an excellent haemostatic effect, thereby preventing clot formation.

Preferably, the electric signal generated by said generator system 12 has a voltage with a peak-to-peak value of approx. 8000V.

The electric signal supplied to active electrode 18 has a periodic, preferably substantially sinusoidal, shape.

In the illustrated embodiment, the electric connection between generator system 12 and handpiece 14 is established by means of an electric cable 13, which allows handpiece 14 to be operated in a remote position or anyway at a distance from generator system 12, as shown by way of example in FIG. 1.

In the illustrated embodiment, handpiece 12 comprises, on the side opposite to end 16, a grip portion 38 that must be held by the operator for directing electrode 18 towards the patient's tissue whereon cut "C" is to be made. In one possible embodiment, said grip portion 38 preferably has an elongated and tapered shape, more preferably an ergonomical shape.

Figure 3:
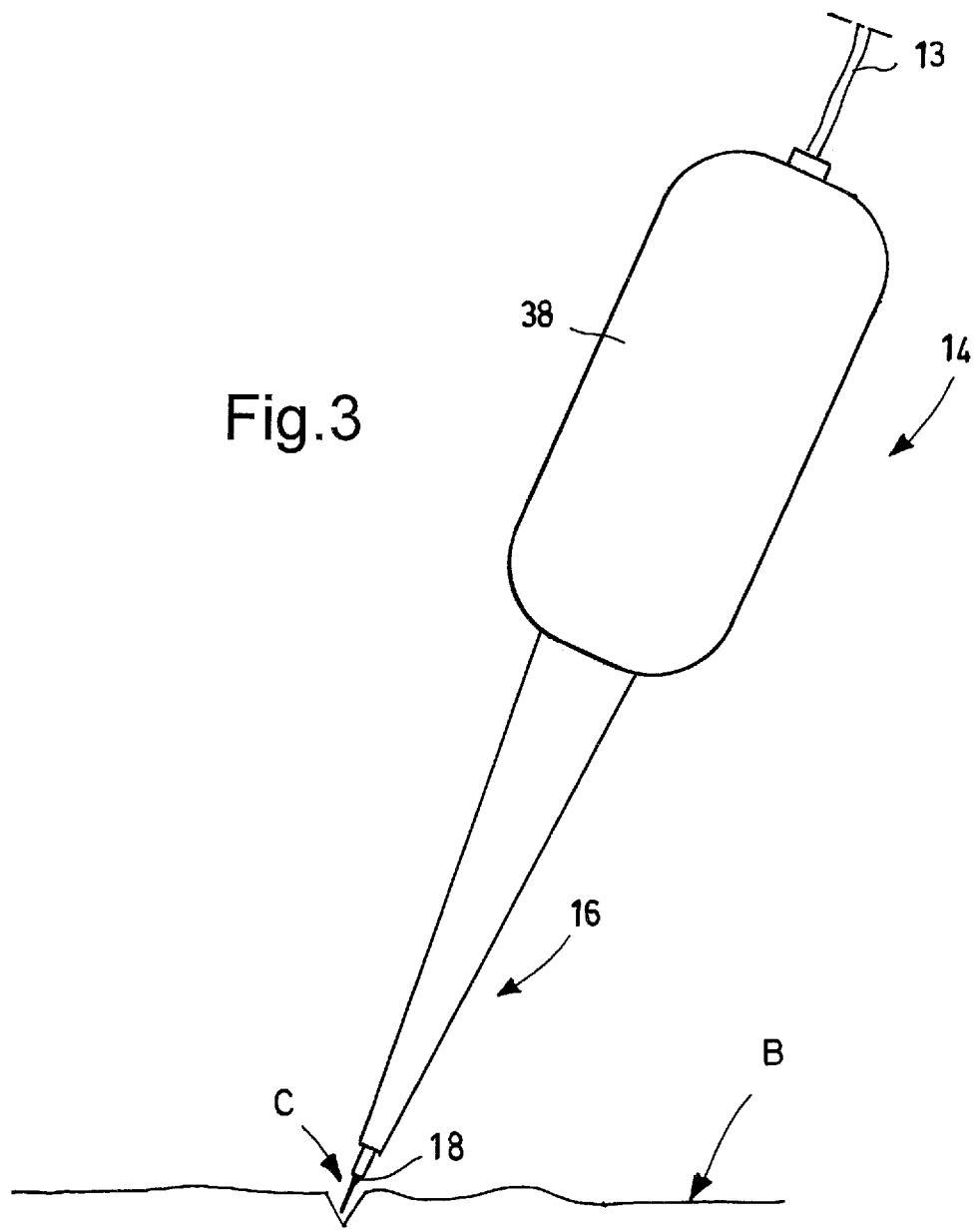
FIG. 3 is a schematic view of the handpiece shown in FIG. 1 during the execution of a cut or an incision on a patient's body.

With particular reference to FIG. 3, there is shown a preferred embodiment of handpiece 14, connected by means of electric cable 13 coming from system 12. Said electric cable 13 is connected to generator system 12 via a connector 201, e.g. as shown in FIG. 1.

With reference to FIG. 1, the apparatus further comprises a regulator device 11, e.g. a pedal regulator, which allows the user to control the signal output towards handpiece 14 for the execution of cut "C".

The same regulator device 11 also performs a safety function by deactivating the signal transmission towards electrode 18 if the same regulator device 11 is not active, e.g. because the same pedal has not been pressed.

Figure 2:
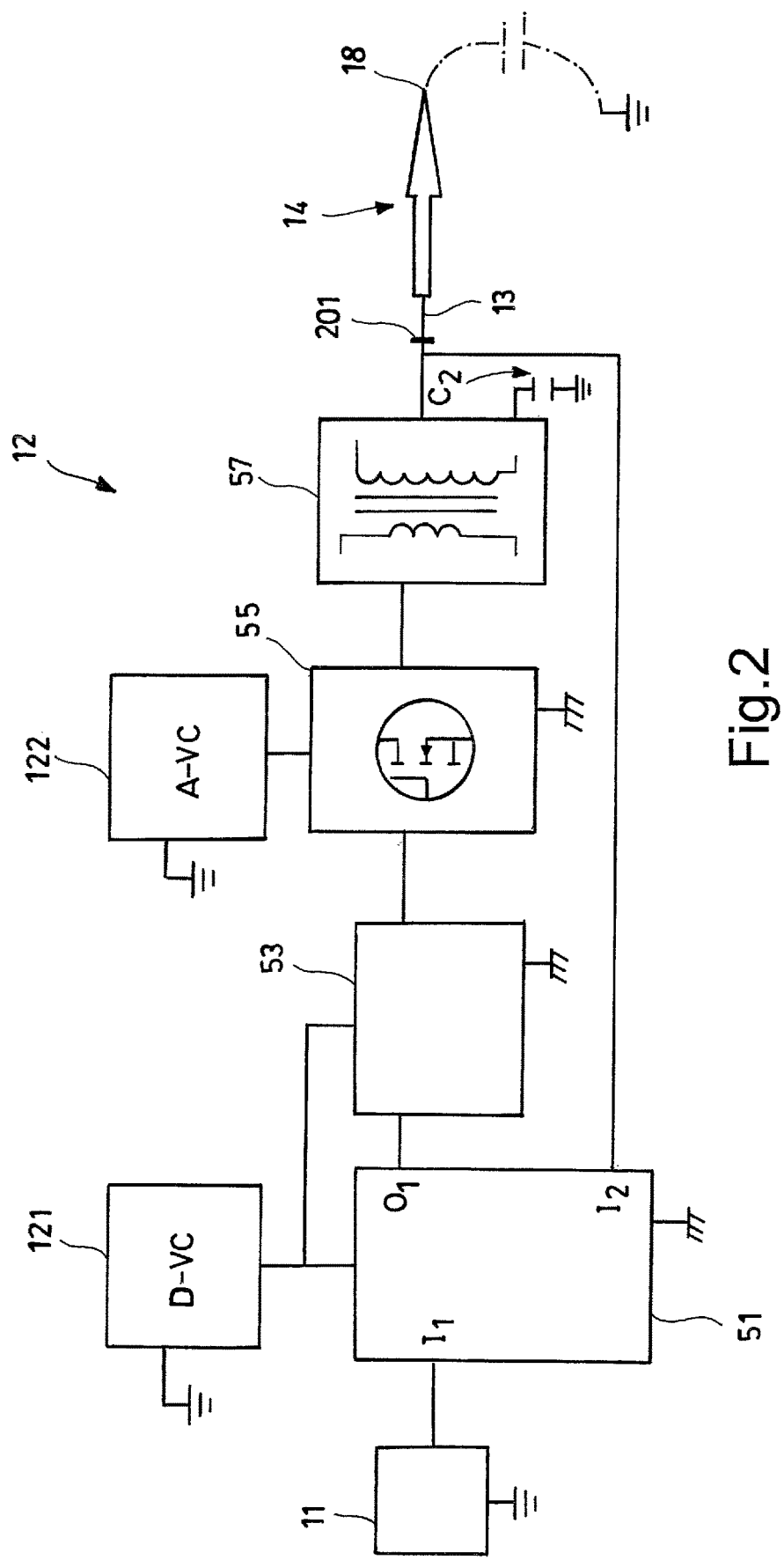
FIG. 2 is a block diagram that generically represents the device of FIG. 1.

Said generator system 12 will be illustrated more in detail below. In one embodiment, as shown by way of illustrative but non-limiting example in FIG. 2, generator system 12 comprises a controller circuit 51, e.g. a microprocessor.

Said controller circuit 51, in addition to performing a computational function and controlling generator system 12, can generate a periodic digital electric signal, e.g. a square-wave signal. The signal can be generated by utilizing an oscillator adapted to generate a clock signal for controller circuit 51. Said oscillator may be either internal, when controller circuit 51 is implemented through a microcontroller, or external, when controller circuit 51 is implemented through a microprocessor.

Said controller circuit 51 is adapted to generate an electric signal at a frequency of 100 kHz.

Preferably, said controller circuit 51 is implemented through a Single Chip microprocessor.

The generator system further comprises a frequency divider 53. Said frequency divider 53 comprises a PLL circuit. According to the present invention, frequency divider 53 can generate an electric signal at a frequency of 50 kHz, starting from the electric signal at 100 kHz generated by said controller circuit 51.

In particular, the 100 kHz electric signal is emitted from an output "O1" of controller circuit 51 and then enters frequency divider 53. At the output of frequency divider 53 there is a periodic digital electronic signal at a frequency of 50 kHz. Said electric signal, e.g. a square-wave signal, is in phase with the 100 kHz signal generated by controller circuit 51, thanks to the PLL circuit included in frequency divider 53.

Continuing the description of generator system 12, the latter comprises a power MOSFET transistor 55.

Said MOSFET transistor 55 is controlled by the electric signal generated by said frequency divider 53.

In one possible embodiment, said MOSFET transistor 55 is an IRF transistor, in particular an IRFP250 transistor.

According to the present invention, generator system 12 comprises both a digital power supply circuit 121, for supplying power to digital devices, such as the controller circuit, and an analogue power supply circuit 122.

Said digital power supply circuit 121 is connected and supplies power to controller circuit 51.

These two power supply circuits (121, 122) are kept distinct and separate from each other to avoid any interference, in particular in the generation of the clock signal of controller circuit 51.

Last, said generator system 12 comprises a transformer circuit 57, preferably a high-frequency transformer.

Said transformer circuit 57 is adapted to provide both a decoupling function and a frequency filtering function for the signal generated by the above-described upstream stages of generator system 12.

Said transformer circuit 57 is configured in such a way that at the terminals of the primary winding there is the following electric connection: at one pole there is a connection to the drain terminal of the MOSFET transistor 55, whereas at the opposite pole there is a connection to said analogue power supply circuit 122.

Said transformer circuit 57 is further configured in such a way that at the terminals of the secondary winding there is the following electric connection: at one pole there is a connection to connector 201, to which handpiece 14 can be connected; whereas at the opposite pole there is a connection to ground through a capacitor.

Preferably, said capacitor is a decoupling capacitor "C2".

Said connector 201 being connectable to one end of electric cable 13, the opposite end of which is connected to handpiece 14.

The use of a transformer grounded by means of a capacitor contributes to avoiding the use of a return plate or second pole for the handpiece. In fact, as aforesaid, apparatus 10 according to the present invention allows making cuts or incisions because its operation is based on the potential difference between active electrode 18 and the tissue of body "B".

Regulator device 11 is also connected to said controller circuit 51, in particular to a terminal "I1", so as to allow the activation of apparatus 10, and in particular the generation of the electric signal to be sent to handpiece 14.

In one possible embodiment, generator system 12 comprises a control circuit 59, which is able to change the parameters of the signal delivered, keeping the level of energy to be delivered to handpiece 14 substantially constant irrespective of the type of tissue on which the apparatus is carrying out the cut.

Control circuit 59 takes a portion of the signal generated by generator system 12, e.g. the signal that is present on the secondary winding of transformer circuit 57, and sends it to controller circuit 51 for a comparison with a predefined value.

Said control circuit 59 carries out a check, in particular a comparison, in particular of the current sent to the handpiece, e.g. present on the secondary winding of transformer circuit 57, and keeps the energy associated with the electric signal generated by generator system 12 and sent to handpiece 14 substantially constant by controlling the electric signals sent to MOSFET transistor 55.

Figure 4:
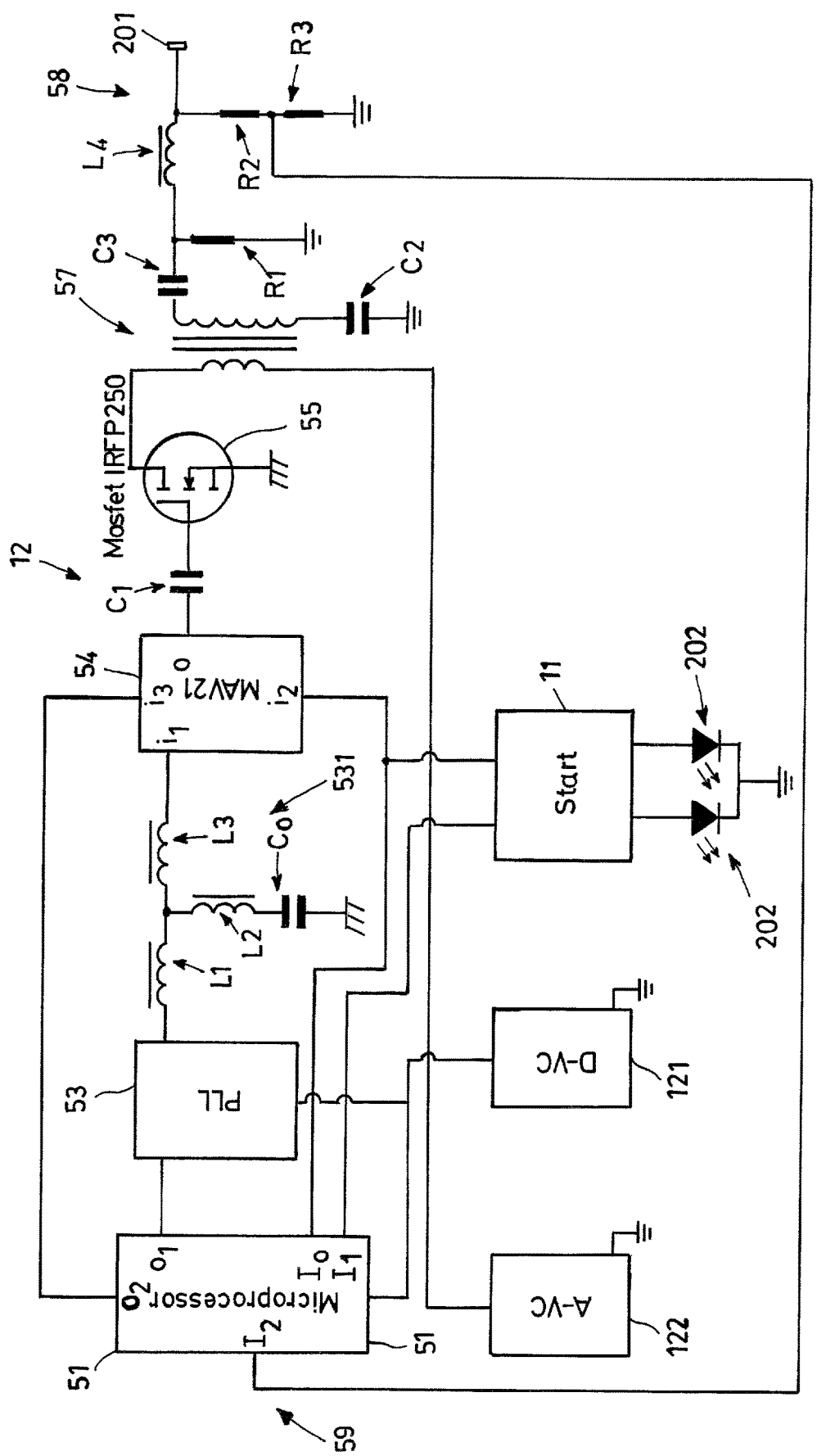
FIG. 4 is a schematic and simplified circuit diagram of the generator according to an illustrative embodiment of the generator system.

Describing more in detail the implementation of one possible exemplary but non-limiting embodiment with reference to FIG. 4, between said frequency divider 53 and said power MOSFET transistor 55 there are: a low-pass filter 531 for suppressing spurious and harmonic frequencies higher than 50 kHz, and an amplifier circuit 54.

Said low-pass filter 531 is preferably a passive filter. In this illustrative embodiment, it is made up of a plurality of inductances (L1, L2, L3), in particular a star configuration of inductances L1, L2 and L3, one terminal is connected to the output of divider circuit 53, a second terminal is connected to an input "i1" of the amplifier circuit 54, and the third terminal of the low-pass filter 531 is connected to ground through a capacitor "C0".

Said one amplifier circuit 54 is adapted to generate a signal having a voltage compatible with the MOSFET standards, for the purpose of correctly driving power MOSFET transistor 55. Said amplifier circuit is implemented through a monolithic device. In an alternative embodiment, said amplifier circuit 54 is implemented by means of discrete components, such as, for example, operational circuits.

In the preferred embodiment, said amplifier circuit 54 is adapted to amplify the signal coming from frequency divider 53, preferably after the filtering executed by low-pass filter 531. Said amplifier circuit can generate a signal having a peak-to-peak voltage of 3V.

Said amplifier circuit 54 is connected to said power MOSFET transistor 55 through a capacitor; in particular, from an output "o" of the amplifier circuit 54 the amplified electronic signal is applied to the gate terminal of the MOSFET transistor through decoupling capacitor "C1".

In summary, MOSFET transistor 55 is connected at the gate terminal to amplifier circuit 54 through a decoupling circuit "C1", at the drain terminal to a pole of the primary winding of transformer circuit 57. The source terminal is connected to ground.

Going on with the illustrative description of one possible embodiment, as shown by way of example in FIG. 4, between a pole of the secondary winding of transformer 57 and said connector 201 there is a band-pass filter 58.

Said band-pass filter 58 has a passband ranging from 35 kHz to 100 kHz, which can eliminate the harmonic frequencies of the electronic signal generated by the upstream devices, as the latter arrives at the secondary winding of transformer circuit 57.

Said band-pass filter 58 is preferably a passive filter. In the exemplary embodiment illustrated herein, it is an RLC filter. The present embodiment includes a capacitor "C3", a resistor "R1", an inductance "L4", e.g. a 600 nH inductance, and a pair of resistors in series "R2" and "R3".

Transformer circuit 57 is preferably a solid-core transformer, e.g. wound on a ferrite core. Also, the transformer comprises a 1 mm air gap.

Transformer circuit 57 has a 1/70 ratio between the primary and secondary windings.

The signal thus processed is then applied to output connector 201 for connection to handpiece 14.

Controller circuit 51 is also connected to regulator device 11 through two terminals "I0" and "I1", which are further configured to provide an astable multivibrator, thus allowing the generation of a reset signal for verifying the proper operation of regulator device 11 by means of feedback elements 20, preferably visual feedback elements 202, such as, for example, LEDs.

The apparatus according to the present invention, in particular said generator system 12, comprises a control circuit 59, which can change the parameters of the electric signal sent to the handpiece, while keeping the energy level constant irrespective of the type of tissue on which the apparatus is carrying out the cut.

Preferably, control circuit 59 can keep the output current and power constant at desired values.

In a preferred embodiment, said control circuit controls the current delivered downstream of the transformer circuit and, by controlling amplifier circuit 54, keeps the power delivered to the handpiece at a substantially constant value.

In one possible embodiment, said controller circuit 51 controls an electric parameter, e.g. current or voltage, preferably voltage, applied to a control input "i3" of amplifier circuit 54. In particular, the voltage at a control output "O2" of controller circuit 51 is adjusted and transferred to said control input "i3" of amplifier circuit 54 in order to regulate, under a constant current condition, the signal output level irrespective of the type of tissue whereon the device is being used.

In general, the value of the energy delivered by handpiece 14 remains substantially constant with different tissues subjected to cutting, even when the type of tissue is changed abruptly.

The present control circuit 59 can further control generator system 12 for adjusting the signal applied to control input "i3" of amplifier circuit 54. The variation of the signal applied to control input "i3" is effected by controller circuit 51, e.g. a microprocessor adapted to control the output level of the signal sent to the handpiece as the parameters under which the handpiece is operating change.

In general, a shunt is used for sampling a signal proportional to the voltage or current value that is present at terminal 201, to which handpiece 14 will be connected. Said signal is then sent to controller circuit 51, which, by comparing said signal with a reference value, can determine a difference between the energy applied to the handpiece and a preset value, in particular an optimal value.

Depending on the difference relative to the preset value, a computation algorithm is used for changing an electric parameter, e.g. the voltage, present at control output "O2" and generated by controller circuit 51, which is applied to control input "i3" of amplifier circuit 54. By varying the electric parameter it is possible to modify the electric signal at output "o" of the amplifier circuit 54, e.g. to modify the gain of the amplifier circuit. The modification of the output signal of amplifier circuit 54 will be reflected in the downstream MOSFET transistor, which will then allow current to flow through the primary winding of transformer circuit 57 as a function of the variation of the electric parameter, e.g. the voltage, applied to the control input "i3" of amplifier circuit 54.

Said preset energy values, e.g. power, voltage and/or current, are stored in a memory unit (not shown), which is connected to controlled device 51. Controller device 51 can retrieve from said memory unit the information necessary for effecting the control as a function of the operating requirements.

With reference to FIG. 4, said band-pass filter 58 comprises two resistors (R2, R3) arranged in series.

An electric signal, e.g. a current or a voltage, more preferably a voltage, is sampled across resistor R3. Said sampled signal is proportional to the signal sent to handpiece 14, once the latter has been connected to connector 201 via cable 13.

Said resistor R3 is preferably a 5 W resistor. The signal sampled across said resistor R3 is applied to an input "I2" of controller circuit 51, preferably a microprocessor.

The received signal is compared with a preset signal. This comparison can be carried out by means of a hardware solution, e.g. through operational circuits, or in software mode, e.g. by programming the microprocessor for executing such operation.

The preferred solution, according to the present invention, is to carry out the comparison by means of a sequence of machine instructions, called Firmware. Preferably, the comparison is made on the signal representing a proportion of the current conducted towards handpiece 14. In particular, control circuit 59 is configured to take a voltage reading across resistor R3. From the voltage reading it is then possible to determine the current flowing through the same resistor R3. The current thus determined is then compared with a predetermined current value, which is optimal for making cut "C".

The difference between the determined current and the optimal current is used by controller circuit 51, in particular a microprocessor, for changing, if necessary, the value of the signal applied to control input "i3" of amplifier circuit 54.

The electronic signal thus generated at a frequency of 100 kHz allows obtaining an electric signal with constant energy at the handpiece by effecting a control in constant current conditions, irrespective of the type of tissue whereon the device is being used, such as, for example, cartilages, poorly conductive tissues, wet tissues, etc.

The present solution ensures a constant energy level during the execution of cut "C" on a tissue of a patient's body.

Preferably, power can be supplied to generator system 12 from an external power source, such as the electric distribution grid, through a power supply unit, preferably of the switching type. In the illustrated embodiment, apparatus 10 is prearranged for receiving power from an electric distribution grid, such as a 220V and 50 Hz alternating current mains. From said external power supply, said digital power supply circuit 121 and said analogue power supply circuit 122 are respectively generated.

In a preferred embodiment, said handpiece 14 comprises electronic components exclusively consisting of an electronic conductor, as it has no control or adjustment devices.

The present solution allows eliminating any devices for directly controlling the signal applied to active electrode 18. The term "control or adjustment devices" refers to power and/or bootstrap switches or push-buttons.

Said handpiece may possibly comprise safety devices, such as, for example, transformers or decouplers, preferably arranged in grip portion 38.

In one possible embodiment, said end 16 can be disconnected from the rest of handpiece 14 for replacement. In a further possible embodiment, the whole handpiece 14 can be disconnected from the electric cable for replacement. In this latter embodiment there is a plug-socket connection between cable 13 and handpiece 14.

The above solutions allow the creation of a low-cost handpiece that can be easily sterilized, while reducing any electric maintenance required on handpiece 14 itself.

Describing more in detail the implementation of apparatus 10 according to the present invention, the same apparatus 10 comprises, as shown in FIG. 1, an external enclosure 101 that separates its components from the outside environment. On at least one face of the same enclosure 101 there are interface elements 20, in particular visual feedback elements 202, such as a display or luminous elements like lamps, preferably LED lamps, and adjustment or activation means 204 including keys and buttons to allow interaction between the user and apparatus 10. Said interface elements 20 are connected to said generator system 12 for receiving or sending information from/to the user.

Said interface elements may possibly comprise audible warning means 203 which, along with visual feedback elements 202, are adapted to detect and signal the proper operation and/or any faults of apparatus 10. Said interface elements 20 may comprise a touch screen.

These aspects of apparatus 10 will not be described any further, since they are known to those skilled in the art.

Likewise, apparatus 10 comprises control means, not shown, for selectively stopping and allowing polarization of active electrode 18 by generator system 12.

As previously specified, apparatus 10 according to the present invention can make a cut "C" on the skin of a patient's body when active electrode 18 comes into contact with the tissue of body "B". If active electrode 18 and the tissue are at a distance not exceeding approx. 2 mm, the signal generated and applied to active electrode 18 will be such as to avoid the formation of a luminescent plasma discharge or arc or the generation of an electric arc, thus preventing any kind of damage to the tissues.

As an alternative to the above, it will be apparent to a man skilled in the art that a different structure may be conceived as concerns said plurality of components comprised in apparatus 10, provided that there is still the possibility of generating and transmitting a periodic (e.g. sinusoidal) signal to at least one active electrode.

Apparatus 10 according to the present invention operates on the basis of the potential difference between electrode 18 and the tissue of body "B". Therefore, should the patient or the operator accidentally come into contact with a metallic mass, such as, for example, metal operating tables, etc., the energy used for producing the ionization and, as a result, the cut or incision "C" will be dispersed in body "B" until the circuit is closed with said metallic mass. This electric dispersion must absolutely be avoided. Therefore, apparatus 10 according to the present invention, comprises a sensor, said sensor is adapted to detect a current leak. If the sensor detects a current leak apparatus 10 will intervene by interrupting energy emission. Preferably, it is the sensor itself that stops energy emission. Preferably, in combination with the interruption of energy emission, or as an alternative to it, apparatus 10 can emit an audible alarm, e.g. through one of said interface elements 20. The sensor thus performs a safety function. The interruption of energy emission occurs in a substantially instantaneous manner, e.g. within 12 μsec from the occurrence of a current leak. The sensor may be calibrated for operating in the presence of a current leak even lower than 80 μA on the patient, e.g. when a current of 40 μA is exceeded.

In the light of the above detailed description, apparatus 10 can operate on tissues which are good electric conductors, e.g. wet tissues, and also on tissues which are bad electric conductors, e.g. bone or cartilage.

Moreover, apparatus 10 is suitable for human and veterinary applications.

Furthermore, it must be pointed out that the Applicant has found that numerous advantages and benefits can be attained from using the apparatus according to the previously described and illustrated embodiment of the present invention, including: fast microcoagulation of the treated region, with low blood loss; substantial absence of burns caused by parasitic RF energy; negligible or null transfer of electromagnetic fields to the human body; negligible or null electric current invasivity; better reactivity to post-surgery recovery times by tissue stimulation.

These advantages cannot be obtained by using traditional devices, wherein frequencies around 500 kHz are used, thus requiring high power levels for making a tissue cut of the same importance as that effected by the apparatus according to the present invention, because the higher the frequency, the less the electric signal will be diffused through the tissue; the lower the frequency irradiated in the tissue, the deeper the signal will be diffused.

Of course, without prejudice to the principle of the invention, the forms of embodiment and the implementation details may be extensively varied from those described and illustrated herein by way of non-limiting example, without however departing from the scope of the invention as set out in the appended claims.

| REFERENCE NUMERALS | |
|---|---|
| Electrosurgical apparatus | 10 |
| External enclosure | 101 |
| Regulator device | 11 |
| Generator system | 12 |
| Digital power supply circuit | 121 |
| Analogue power supply circuit | 122 |
| Electric cable | 13 |
| Handpiece | 14 |
| End | 16 |
| Active electrode | 18 |
| Interface elements | 20 |
| Connector | 201 |
| Visual feedback elements | 202 |
| Warning means | 203 |
| Grip portion | 38 |
| Controller circuit | 51 |
| Terminal | I0 |
| Terminal | I1 |
| Input | I2 |
| Output | O1 |
| Control output | O2 |
| Frequency divider | 53 |
| Low-pass filter | 531 |
| Inductance | L1 |
| Inductance | L2 |
| Inductance | L3 |
| Capacitor | C0 |
| Amplifier circuit | 54 |
| Input | i1 |
| Terminal | i2 |
| Control input | i3 |
| Output | o |
| Capacitor | C1 |
| Power MOSFET transistor | 55 |
| Transformer circuit | 57 |
| Capacitor | C2 |
| Band-pass filter | 58 |
| Capacitor | C3 |
| Resistor | R1 |
| Resistor | R2 |
| Inductance | L4 |
| Control circuit | 59 |
| Resistor | R3 |
| Body | B |
| Cut or incision | C |

The invention claimed is:

1. An electrosurgical apparatus for performing a tissue cut or incision on a body of a human or animal patient, said apparatus comprising:
   a generator system, configured to generate a radio-frequency electric signal; and
   a hand-piece, to be held by an operator and comprising an end, which is provided with a single active electrode electrically connected to said generator system;
   said generator system being configured to generate said electric signal, which produces said cut or incision when said active electrode comes into contact with tissue of the body of the human or animal patient, due to a thermal effect;
   said generator system being configured to generate said electric signal having:
      a power ranging from 0.5 W to 20 W;
      a frequency ranging from 40 kHz to 90 kHz;
      said generator system being configured to generate said electric signal so that:

energy emitted is transferred from the active electrode to the tissue of the body through capacitive coupling;

the tissue cut is performed at a peripheral temperature ranging from 45° C. to 60° C.;

the apparatus being configured so that, while the cut is being performed, a resulting electric circuit is closed to ground through a capacitive effect, free of use of a return plate;

wherein said generator system comprises:

a controller circuit for generating a digital electric signal at a frequency of 100 kHz;

a frequency divider comprising a phase-locked loop (PLL) circuit, for generating said digital electric signal at a frequency of 50 kHz starting from the digital electric signal at 100 kHz generated by said controller circuit;

a power MOSFET transistor, controlled by the digital electric signal generated by said frequency divider;

a digital power supply circuit for supplying power to the controller circuit, the frequency divider and/or power transistor;

an analog power supply circuit; and a transformer circuit configured so that;

a first electrical connection and a second electrical connection are at terminals of a primary winding;

at one pole of the primary winding the first electrical connection connects to a drain terminal of the MOSFET transistor, at an opposite pole of the primary winding the second electrical connection connects to said analog power supply circuit;

a third electrical connection and a fourth electrical connection are at terminals of a secondary winding;

at one pole of the secondary winding the third electrical connection connects to a connector to which the hand-piece is connectable;

wherein at an opposite pole of the second winding the fourth electrical connection connects to ground through a capacitor.

2. An apparatus according to claim 1, wherein said generator system is adapted to generate said electric signal having the following parameters:

a current intensity of approximately 0.0005 A, a frequency of approximately 50 kHz, and a duty cycle duration approximately ranging from 10 µs to 30 s.

3. An apparatus according to claim 1, comprising between said frequency divider and said power MOSFET transistor:

a low-pass filter, for suppressing spurious or harmonic frequencies exceeding 50 kHz;

an amplifier circuit, for generating a distinct signal with a voltage compatible with MOSFET standards; said amplifier circuit is connected to said power MOSFET transistor through a distinct second capacitor.

4. An apparatus according to claim 3, wherein said generator system comprises a control circuit configured to change parameters of the radio-frequency electric signal delivered, keeping a level of energy to be delivered to the hand-piece substantially constant irrespective of a type of tissue on which the apparatus is carrying out the cut.

5. An apparatus according to claim 4, wherein the control circuit samples a portion of the electric signal generated by the generator system and sends the portion of the electric signal sampled to the controller circuit for a comparison with a predefined value.

6. An apparatus according to claim 4, wherein said control circuit carries out a comparison of current sent to the hand-piece and, by controlling said amplifier circuit, keeps the energy associated with the electric signal generated by the generator system substantially constant.

7. An apparatus according to claim 4, wherein said control circuit carries out a comparison of current sent to the hand-piece and, by controlling said amplifier circuit, keeps the energy associated with the electric signal generated by the generator system substantially constant.

8. An apparatus according to claim 1, wherein at the third electrical conductor between the pole of the secondary winding of the transformer and said connector is a band-pass filter with a passband ranging from 35 kHz to 100 kHz, which is configured to eliminate harmonic frequencies of the electric signal generated by the generator system.

9. An apparatus according to claim 1, wherein said transformer circuit is a high-frequency transformer, with a solid core and an air gap, and a 1/70 ratio between the primary winding and the secondary winding.

10. An apparatus according to claim 9, wherein said hand-piece comprises electronic components exclusively consisting of an electronic conductor, as it has no control or adjustment devices.

11. An apparatus according to claim 1, wherein the generator system comprises a control circuit;

said control circuit being adapted to keep output current and power constant irrespective of a type of tissue on which the apparatus is carrying out the cut.

* * * * *